United States Patent [19]
Incavo et al.

[11] Patent Number: 6,156,070
[45] Date of Patent: Dec. 5, 2000

[54] ALLOGRAFT PROSTHETIC JOINTS AND METHOD

[75] Inventors: Stephen J. Incavo, South Burlington, Vt.; Martin M. Coyne, III, Harrington Park; Andrij J. Nedilsky, New Milford, both of N.J.

[73] Assignee: Howmedica Osteonics Corp., Allendale, N.J.

[21] Appl. No.: 09/277,672

[22] Filed: Mar. 26, 1999

[51] Int. Cl.[7] ................................. A61F 2/36; A61F 2/32
[52] U.S. Cl. .................... 623/23.52; 623/23.15; 623/16.11; 623/23.61; 623/23.28
[58] Field of Search .............. 623/16.11, 18.11, 623/20.16, 20.17, 20.35, 23.15, 23.23, 23.26, 23.28, 23.29, 23.36, 23.51, 23.52, 23.6, 23.61

[56] References Cited

U.S. PATENT DOCUMENTS

| | | |
|---|---|---|
| 3,906,550 | 9/1975 | Rostoker et al. . |
| 4,950,296 | 8/1990 | McIntyre . |
| 5,035,714 | 7/1991 | Willert et al. . |
| 5,053,049 | 10/1991 | Campbell . |
| 5,061,286 | 10/1991 | Lyle . |
| 5,112,354 | 5/1992 | Sires . |
| 5,133,772 | 7/1992 | Hack et al. . |
| 5,258,034 | 11/1993 | Furlong et al. . |
| 5,458,653 | 10/1995 | Davidson . |
| 5,480,451 | 1/1996 | Grundei et al. . |
| 5,490,853 | 2/1996 | Burkinshaw et al. . |
| 5,571,193 | 11/1996 | Kampner . |
| 5,697,932 | 12/1997 | Smith et al. . |
| 5,814,084 | 9/1998 | Grivas et al. . |

FOREIGN PATENT DOCUMENTS

| | | | |
|---|---|---|---|
| 0378044 | 7/1990 | European Pat. Off. | 623/23 |
| 0623321 | 11/1994 | European Pat. Off. | 623/23 |
| 2666984 | 3/1992 | France | 623/23 |

OTHER PUBLICATIONS

S.J. Incavo et al, "Allograft–Host Mismatch in Revision Total Hip Replacement" *Orthopaedic Review*, Oct. 1994, 832–36.

*Primary Examiner*—David J. Isabella
*Attorney, Agent, or Firm*—Arthur Jacob

[57] ABSTRACT

A prosthetic implant for replacing an element of a natural joint includes an elongate core for securing the implant within natural bone at an implant site adjacent the natural joint, the implant including a allograft affixed to the core for interposition between the core and the natural bone at the implant site. A kit of component parts enables a surgeon to select allograft component parts for assembly with the core, interoperatively, for accommodating conditions encountered at the implant site.

29 Claims, 5 Drawing Sheets

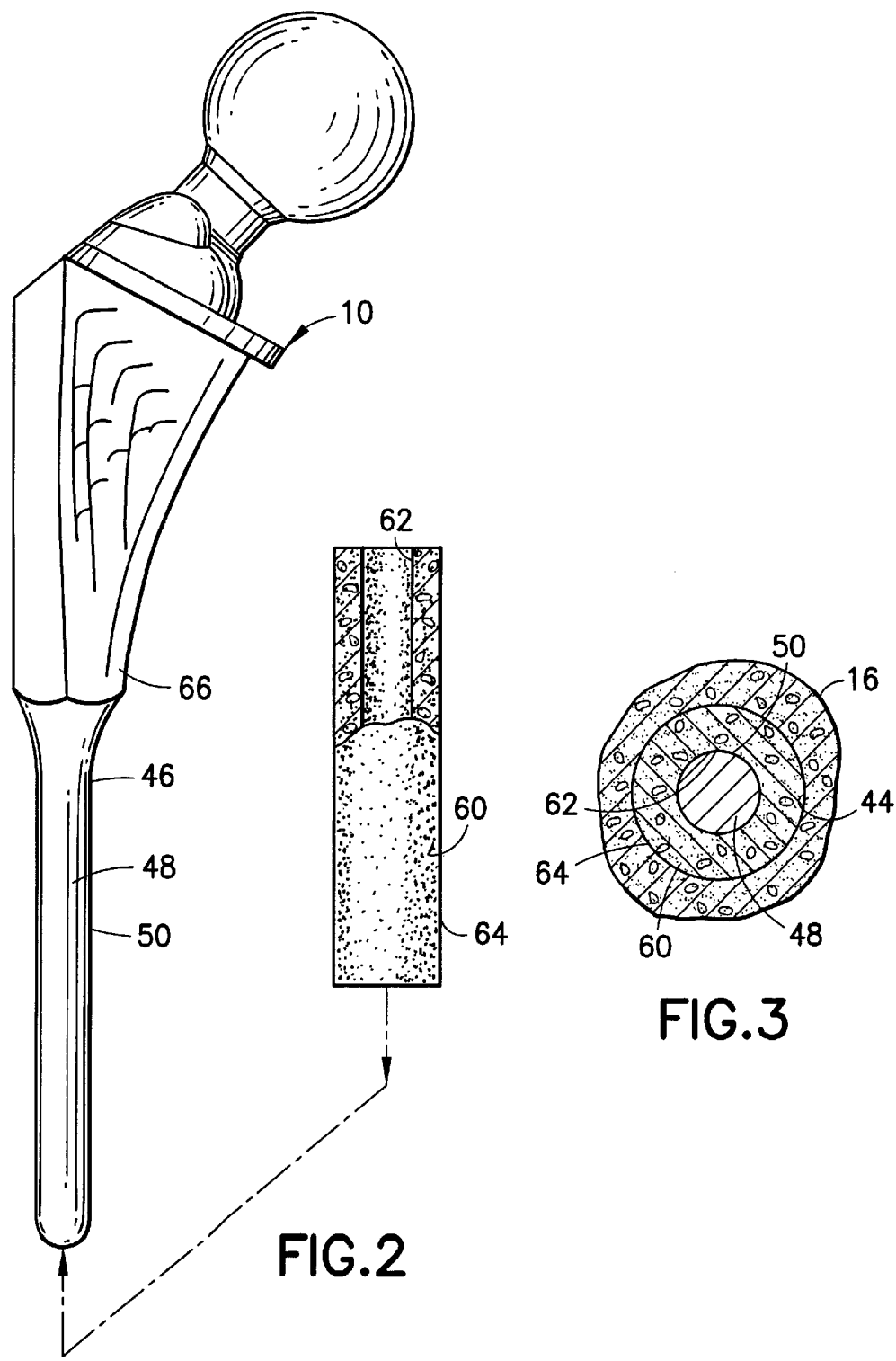

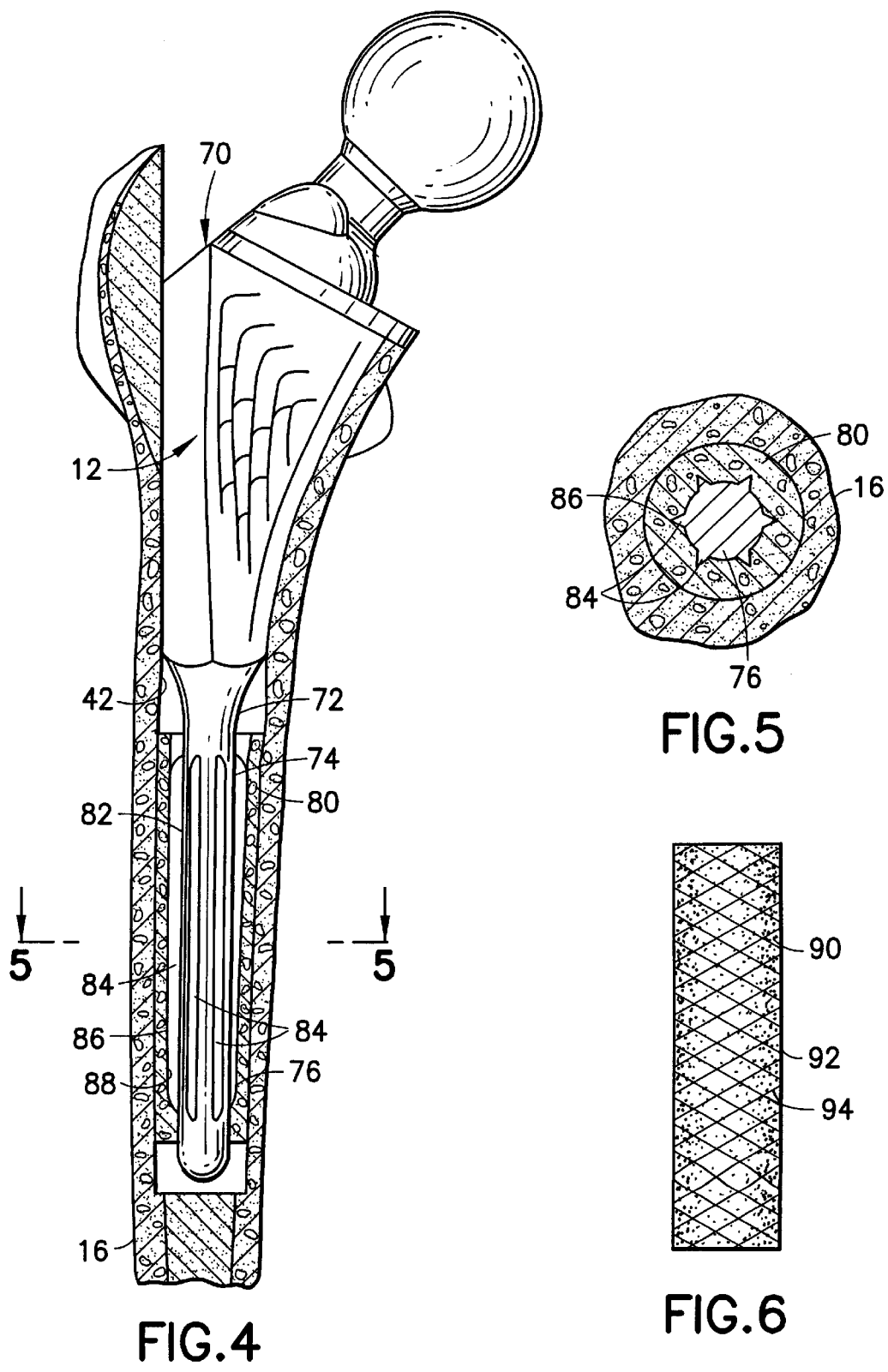

ALLOGRAFT PROSTHETIC JOINTS AND METHOD

The present invention relates generally to the replacement of natural joints of the body with prosthetic implants and pertains, more specifically, to the employment of allograft components in such prosthetic implants and procedures.

Deficiencies in natural bone encountered at particular implant sites present a very real challenge to a surgeon seeking to implant a prosthetic joint at such a site. While such deficiencies can be the result of severe injury or disease at a particular joint, deficiencies in natural bone frequently are encountered in revision surgery, where previously implanted prosthetic joint components must be removed and replaced. A site which exhibits these deficiencies may not be capable of supporting a conventional implant component with sufficient stability and structural integrity.

The use of allografts to supplement natural bone available at the site of a skeletal repair where the site suffers from a deficiency of natural bone is receiving increased interest. The present invention enables the employment of allografts and allograft techniques in connection with the replacement of natural joints in the body with prosthetic implants, where the site of the implant is deficient in natural bone. As such, the present invention attains several objects and advantages, some of which are summarized as follows: Enables successful replacement of a natural joint at a site in the body which suffers from a more severe deficiency in natural bone; facilitates revision surgery wherein a previously implanted prosthetic joint component is removed and replaced; provides a surgeon with a wider range of options in replacing a joint at a bone deficient site in the body; enables increased versatility in either the initial replacement of a natural joint or in a revision; increases accuracy in effecting replacement of a natural joint; provides increased stability and structural integrity at an implant site; provides a prosthetic implant of more desirable structure and composition for accommodating a wider variety of conditions encountered at an implant site; provides a prosthetic implant which exhibits exemplary performance over an extended service life.

The above objects and advantages, as well as further objects and advantages, are attained by the present invention which may be described briefly as a prosthetic implant having a proximal portion for enabling replacement of an element of a natural joint, and a distal portion for securement within a recess in the natural bone adjacent the natural joint, the recess including an internal surface, the prosthetic implant comprising: an elongate core extending axially along the distal portion of the prosthetic implant for reception within the recess in the natural bone, the core having an external surface for confronting the internal surface of the recess in the natural bone and being spaced from the internal surface when the core is located within the recess; and at least one allograft for placement along the core, over the external surface of the core, for interposition between the core and the internal surface of the recess, the allograft having a generally tubular configuration including an inner securement surface for gripping the core to secure the allograft in place upon the core and an outer locator surface for engaging the internal surface of the recess to locate the core transversely within the recess.

In addition, the present invention includes a kit of component parts for assembling a prosthetic implant, the prosthetic implant having a proximal portion for enabling replacement of an element of a natural joint, and a distal portion for securement within a recess in the natural bone adjacent the natural joint, the recess including an internal surface, the kit of component parts comprising: a first component part having an elongate core extending axially to establish the distal portion of the prosthetic implant for reception within the recess in the natural bone, the core having an external surface for confronting the internal surface of the recess in the natural bone and being spaced from the internal surface when the core is located within the recess; and at least one second component part in the form of an allograft to be placed on the core, over the external surface of the core, for interposition between the core and the internal surface of the recess, the allograft having a generally tubular configuration including an inner securement surface for gripping the core to secure the allograft in place upon the core and an outer locator surface for engaging the internal surface of the recess to locate the core transversely within the recess.

Further, the invention provides an improvement in a method for implanting a prosthetic implant having a proximal portion for enabling replacement of an element of a natural joint, and a distal portion for securement within a recess in the natural bone adjacent the natural joint, the recess including an internal surface, the method comprising the steps of: providing an elongate core extending axially along the distal portion of the prosthetic implant for reception within the recess in the natural bone, the core having an external surface for confronting the internal surface of the recess in the natural bone and being spaced from the internal surface when the core is located within the recess; providing at least one allograft for placement along the core, over the external surface of the core; and placing at least the one allograft for interposition between the core and the internal surface of the recess, the allograft having a generally tubular configuration including an inner securement surface for gripping the core to secure the allograft in place upon the core and an outer locator surface for engaging the internal surface of the recess to locate the core transversely within the recess.

In addition, the invention provides a method for assembling a prosthetic implant having a proximal portion for enabling replacement of an element of a natural joint, and a distal portion for securement within a recess in the natural bone adjacent the natural joint, the recess including an internal surface, the method comprising: providing an elongate core extending axially along the distal portion of the prosthetic implant for reception within the recess in the natural bone, the core having an external surface for confronting the internal surface of the recess in the natural bone and being spaced from the internal surface when the core is located within the recess; providing at least one allograft for placement on the core, over the external surface of the core; placing at least the one allograft on the core for interposition between the core and the internal surface of the recess, the allograft having a generally tubular configuration including an inner securement surface for confronting the core and an outer locator surface for engaging the internal surface of the recess to locate the core transversely within the recess; and affixing the selected allograft to the core.

The invention will be understood more fully, while still further objects and advantages will become apparent, in the following detailed description of preferred embodiments of the invention illustrated in the accompanying drawing, in which:

FIG. 2 is an exploded elevational view of the component;

FIG. 3 is an enlarged cross-sectional view taken along line 3—3 of FIG. 1;

FIG. 4 is a partially sectioned elevational view of an alternate prosthetic implant component;

FIG. 5 is an enlarged cross-sectional view taken along line 5—5 of FIG. 4;

FIG. 6 is an elevational view of an alternate part of the component;

Figure 1:
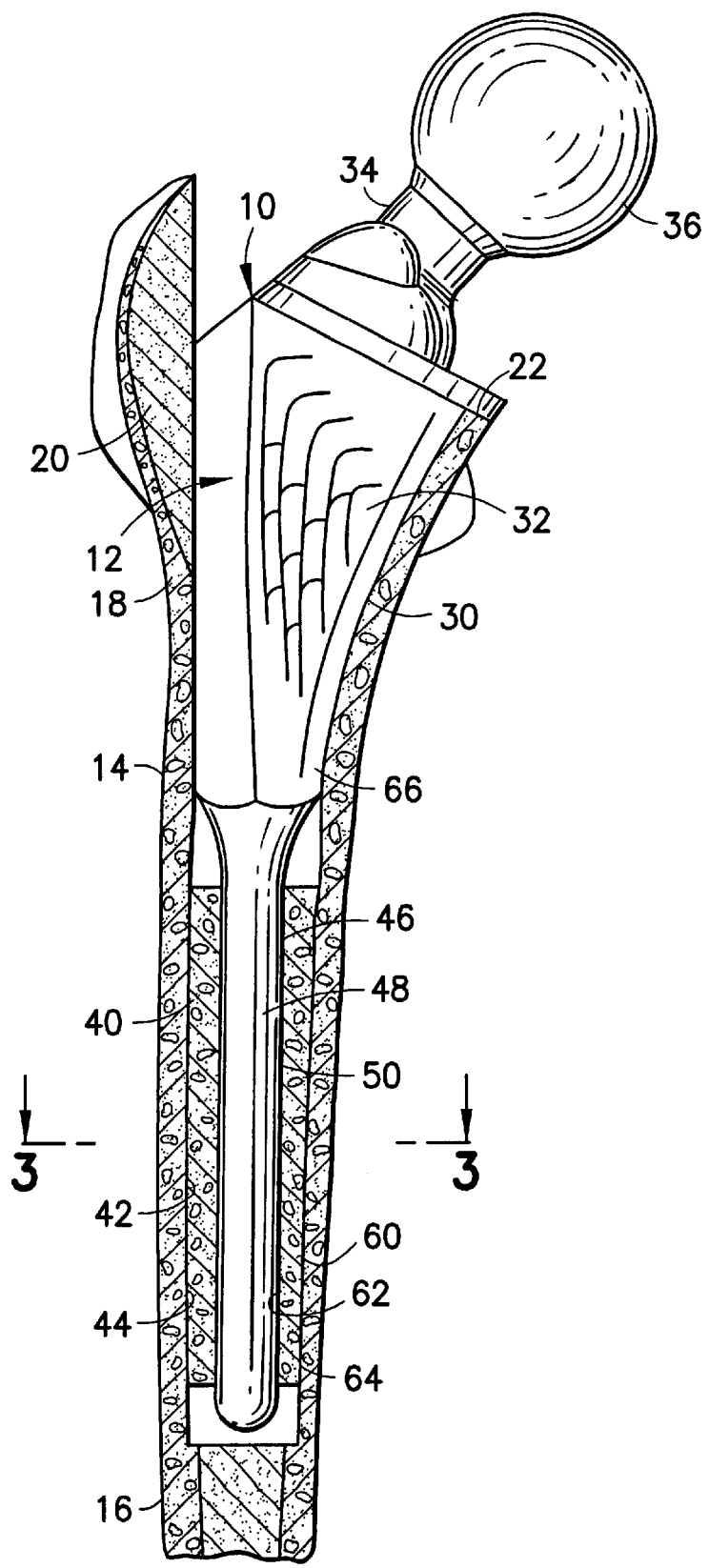
FIG. 1 is a partially sectioned elevational view showing a prosthetic implant component constructed in accordance with the invention and implanted within a natural bone.

Referring now to the drawing, and especially to FIG. 1 thereof, the present invention is illustrated in connection with the replacement of a natural hip joint with a prosthetic hip joint which includes a femoral component shown at 10. Femoral component 10 is shown implanted at an implant site 12 in the proximal femur 14 of a natural femur 16 having an outer shell of cortical bone 18, inner cancellous bone 20 and calcar 22. The illustrated site 12 is deficient in natural bone; that is, as a result of either injury or disease, or revision surgery, the natural bone available at the site 12 is inadequate to support a conventional femoral component of a replacement hip joint with sufficient stability and desirable structural integrity and composition. Femoral component 10 is constructed in accordance with the present invention and provides a reliable and effective component for implant at site 12.

Thus, femoral component 10 has a proximal portion 30 which includes an affixation surface 32 and a neck 34 for carrying a selectively attached spherical head 36, which replaces a natural element of the natural hip joint, for engagement with either the natural acetabulum or an acetabular prosthesis for articulation in a hip replacement, all in a now conventional manner. A distal portion 40 is provided for securement within a recess 42 in the natural bone of the femur 16, adjacent the joint being replaced. As illustrated, the recess 42 has an internal surface 44 and is relatively large, extending transversely into the cortical bone 18, as a result of the site 12 being deficient in natural bone, leaving relatively less natural bone for support of the femoral component 10. In order to establish adequate support for the femoral component 10 at site 12, the distal portion 40 has a stem 46 which includes an elongate core 48 extending axially along the distal portion 40 and received within the recess 42. The core 48 has a generally cylindrical configuration and includes an external surface 50 spaced transversely from and confronting the internal surface 44 of the recess 42. While the larger dimensions of recess 42 could be accommodated with a femoral component of conventional construction, such a conventional construction would include a stem of corresponding larger dimensions resulting in undesirable stiffness and concomitant undesirable loading of the natural bone.

An allograft is shown in the form of a sleeve 60 of natural bone interposed between the core 48 and the internal surface 44 of the recess 42. Sleeve 60 has a generally tubular configuration which includes an annular cross-sectional configuration and an inner securement surface 62 for gripping the core 48, along the external surface 50, to secure the sleeve 60 in place upon the core 48. An outer locator surface 64 engages the internal surface 44 of the recess 42 and locates the core 48 transversely within the recess 42. The preferred material for the proximal portion 30 of the femoral component 10 is a biocompatible metal, such as titanium or a titanium alloy, and core 48 also is constructed of that preferred material; however, in order to attain effective support and securement of the femoral component 10 at bone deficient site 12, the core 48 is reduced in radial, or transverse dimensions, relative to the radial, or transverse extent of recess 42, so as to enable the interposition of the allograft in the form of sleeve 60. Thus, femoral component 10 is comprised of assembled component parts, including a metallic component part 66, which includes the proximal portion 30 and core 48, the spherical head 36, and the allograft in the form of sleeve 60. The natural bone of the allograft provided by sleeve 60 will incorporate over time with the natural bone existing at the site 12, for establishing a bone structure adequate to support the femoral component 10 at the site 12. In addition, use of the allograft provides a more flexible prosthetic construct for desirable loading characteristics. Further, incorporation of the allograft will increase the amount of natural bone available for long-term performance, as well as for any additional surgical procedures which may become necessary. The natural bone of the sleeve 60 may be supplemented, if desired, with growth factors or medicaments.

As best seen in FIGS. 2 and 3, as well as in FIG. 1, subsequent to preparing the proximal femur for the reception of the femoral component 10, a sleeve 60 of appropriate dimensions is selected for location along the core 48 of the femoral component 10. In the preferred procedure, the selected sleeve 60 is slipped over the core 48 and secured in place on the core 48 prior to inserting the assembled sleeve 60 and core 48 into the recess 42. In the preferred practice of the present invention, a surgeon is provided with a kit of component parts which, in addition to including a selection of component parts 66 and spherical heads 36 of different sizes, includes a plurality of sleeves 60 having different dimensions so as to enable the selection of a sleeve 60, interoperatively, for assembly with the core 48 of a selected component part 66 to accommodate the particular prepared recess 42 at the implant site 12. The relative dimensions of the external surface 50 of the core 48 and the inner securement surface 62 of each sleeve 60 is such that upon engagement of the selected sleeve 60 with the core 48, the sleeve 60 grips the core 48 and is secured in place upon the core 48.

Turning now to FIGS. 4 and 5, an alternate femoral component 70 is constructed in a manner similar to femoral component 10, and includes a distal portion 72 with a stem 74 having an elongate core 76 which carries an allograft in the form of a sleeve 80 affixed to the core 76. In order to enhance the securement of the sleeve 80 on the core 76, the external surface 82 of the core 76 is provided with projections illustrated in the form of splines 84 extending transversely from the external surface 82 to pointed crests 86, and extending axially along the core 76 to engage the inner securement surface 88 of the sleeve 80 and secure the sleeve 80 against movement along the core 76 when the sleeve 80 is in place on the core 76. The engagement of the splines 84 with the sleeve 80 assures that in the preferred procedure the sleeve 80 is secured in place upon the core 76 prior to insertion of the core 76 into the recess 42 of the proximal femur and remains in place during insertion of the core 76 into the recess 42 and proper seating of the femoral component 70 at the implant site 12.

In the alternate embodiment illustrated in FIG. 6, a sleeve 90 is constructed similar to sleeves 60 and 80; however, in order to enhance the engagement of the outer locator surface 92 of the sleeve 90 with the internal surface 44 of the recess 42 (see FIG. 1), and to promote incorporation along the engaged outer locator surface 92 of the sleeve 90 and the internal surface 44 of the recess 42, the outer locator surface 92 is textured, as by knurling or the like as shown at 94.

Figure 7:
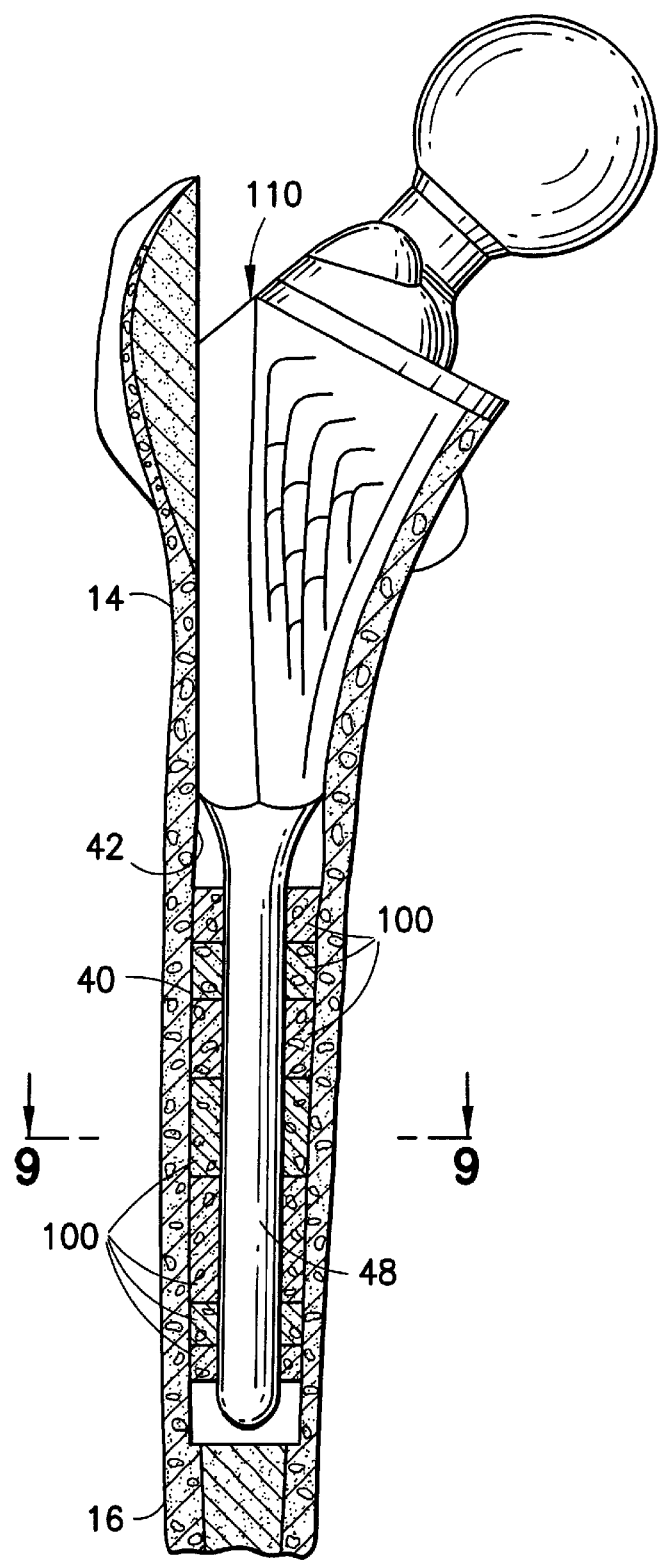
FIG. 7 is a partially sectioned elevational view of another alternate prosthetic implant component.
Figure 8:
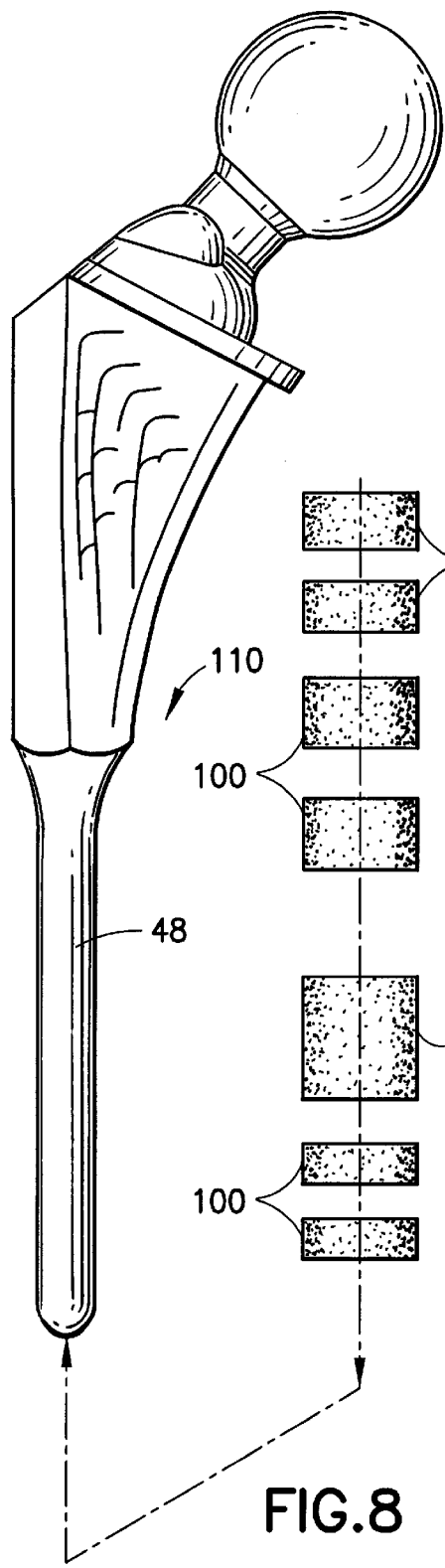
FIG. 8 is an exploded elevational view of the component of FIG. 7.
Figure 9:
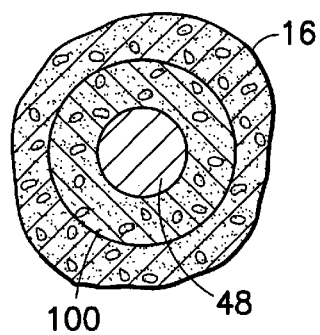
FIG. 9 is an enlarged cross-sectional view taken along line 9—9 of FIG. 7.

Referring now to FIGS. 7 through 9, in another alternate embodiment a plurality of allografts are provided in the form of a plurality of sleeves 100 each having an axial length relatively shorter than the sleeves 60, 80 and 90 described above. Selected sleeves 100 are strung upon the core 48 of the distal portion 40 to establish an alternate femoral component 110 in which the full allograft is in the form of a plurality of sleeves 100 affixed to the core 48. The ability to select multiple sleeves 100 from a plurality of such sleeves 100 supplied in a kit of component parts enables a surgeon to accommodate, interoperatively, a variety of conditions encountered at particular implant sites. For example, variations in transverse dimensions of the recess 42 along the axial extent of core 48 can be accommodated by placing sleeves 100 of different transverse dimensions at different axial locations along the core 48. Likewise, differences in axial length can be accommodated interoperatively by selecting sleeves 100 of appropriate length. Further, allografts provided in the form of shorter sleeves 100 are more readily available. The selected sleeves 100 preferably are affixed to the core 48 prior to insertion of the core 48 into the prepared recess 42 in the proximal femur 14, as described above.

Figure 10:
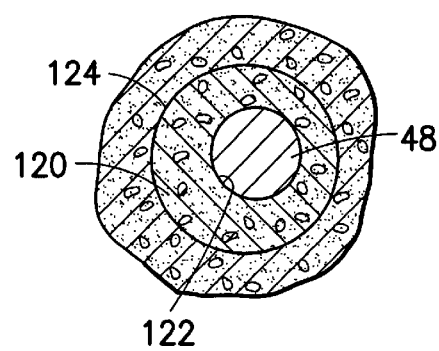
FIG. 10 is a cross-sectional view similar to FIG. 9 and showing another embodiment of the invention.
Figure 11:
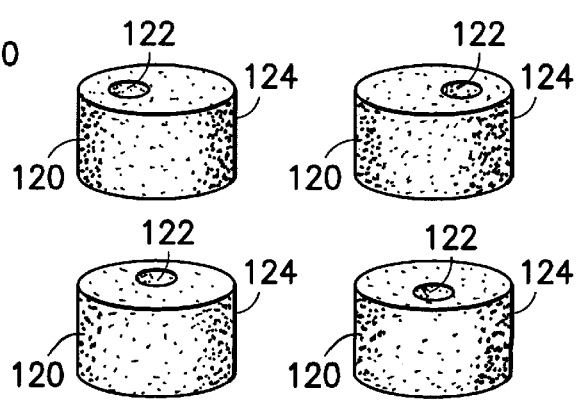
FIG. 11 is a pictorial perspective view of a plurality of component parts in a kit of component parts for use in connection with the embodiment of FIG. 10.

In the alternate embodiment illustrated in FIGS. 10 and 11, a plurality of sleeves 120 each include an inner securement surface 122 and an outer locator surface 124; however, rather than being concentric, the inner securement surface 122 and the outer locator surface 124 are eccentric so as to be offset relative to one another. In this manner, a surgeon is provided with further interoperative options for accommodating conditions encountered at a particular implant site. For example, should the proximal femur be curved along the length of the femur, the surgeon may select and assemble sleeves 120 upon core 48 oriented so as to conform the composite contour of the outer locator surfaces 124 of the selected sleeves 120 to the curved configuration of the recess within which the stem of the femoral component is to be inserted.

While the illustrated embodiments pertain to femoral components of hip replacements, it will be apparent that similar constructs are available for prosthetic implants which enable the replacement of elements of other natural joints, such as knee joints, shoulder joints and others.

It will be seen that the present invention attains all of the objects and advantages summarized above, namely: Enables successful replacement of a natural joint at a site in the body which suffers from a more severe deficiency in natural bone; facilitates revision surgery wherein a previously implanted prosthetic joint component is removed and replaced; provides a surgeon with a wider range of options in replacing a joint at a bone deficient site in the body; enables increased versatility in either the initial replacement of a natural joint or in a revision; increases accuracy in effecting replacement of a natural joint; provides increased stability and structural integrity at an implant site; provides a prosthetic implant of more desirable structure and composition for accommodating a wider variety of conditions encountered at an implant site; provides a prosthetic implant which exhibits exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in a prosthetic implant having a proximal portion for enabling replacement of an element of a natural joint, and a distal portion for securement within a recess in the natural bone adjacent the natural joint, the recess including an internal surface having a transverse extent, the improvement comprising:

an elongate core extending axially along the distal portion of the prosthetic implant for reception within the recess in the natural bone, the core having an external surface with a transverse dimension less than the transverse extent of the internal surface of the recess for confronting the internal surface of the recess in the natural bone with the external surface spaced from the internal surface when the core is located within the recess; and at least one allograft body along the core, over the external surface of the core, for interposition between the core and the internal surface of the recess, the allograft body having a generally tubular configuration including an inner securement surface gripping the core to secure the allograft body in place upon the core and an outer locator surface for engaging the internal surface of the recess to locate the core transversely within the recess.

2. The invention of claim 1 wherein the core has a generally cylindrical configuration and the allograft body has an annular configuration, with the inner securement surface and the outer locator surface being generally cylindrical surfaces.

3. The invention of claim 1 including a plurality of allograft bodies for placement along the core.

4. The invention of claim 1 wherein the outer locator surface includes a textured structure.

5. The invention of claim 1 including projections on the external surface of the core, the projections extending transversely for engaging the allograft body to secure the allograft body against movement relative to the core when the allograft body is in place upon the core.

6. The invention of claim 5 wherein the projections comprise splines extending axially along the core.

7. The invention of claim 1 wherein the recess is in the natural bone of a femur and the prosthetic implant is a femoral hip prosthesis having a stem for placement in the recess, the proximal portion enables replacement of a femoral heads the distal portion includes the stem, and the elongate core extends along the stem.

8. A kit of component parts for assembling a prosthetic implant, the prosthetic implant having a proximal portion for enabling replacement of an element of a natural joint, and a distal portion for securement within a recess in the natural bone adjacent the natural joint, the recess including an internal surface having a transverse extent, the kit of component parts comprising:

a first component part having an elongate core extending axially to establish the distal portion of the prosthetic implant for reception within the recess in the natural bone, the core having an external surface with a transverse dimension less than the transverse extent of the internal surface of the recess for confronting the internal surface of the recess in the natural bone with the external surface spaced from the internal surface when the core is located within the recess; and at least one second component part in the form of an allograft body to be placed on the core, over the external surface of the core, for interposition between the core and the internal surface of the recess, the allograft body having a generally tubular configuration including an inner securement surface for gripping the core to secure the allograft body in place upon the core and an outer locator surface for engaging the internal surface of the recess to locate the core transversely within the recess.

9. The invention of claim 8 wherein the core has a generally cylindrical configuration and the allograft body has an annular configuration, with the inner securement surface and the outer locator surface being generally cylindrical surfaces.

10. The invention of claim 8 including a plurality of second component parts comprising a plurality of allograft bodies for selective placement upon the core.

11. The invention of claim 10 wherein the relative transverse location of the inner and outer surfaces of at least one of the plurality of allograft bodies differs from the relative transverse location of the inner and outer surfaces of another of the plurality of allograft bodies for enabling selection of one or another of the plurality of allograft bodies for placement on the core.

12. The invention of claim 8 wherein the outer locator surface includes a textured structure.

13. The invention of claim 8 including projections on the external surface of the core, the projections extending transversely for engaging the allograft body to secure the allograft against movement relative to the core when the allograft body is in place upon the core.

14. The invention of claim 13 wherein the projections comprise splines extending axially along the core.

15. The invention of claim 8 wherein the recess is in the natural bone of a femur and the prosthetic implant is a femoral hip prosthesis having a stem for placement in the recess, the proximal portion enables replacement of a femoral heads the distal portion includes a stem, and the elongate core extends along the stem.

16. In a method for implanting a prosthetic implant having a proximal portion for enabling replacement of an element of a natural joint, and a distal portion for securement within a recess in the natural bone adjacent the natural joint, the recess including an internal surface having a transverse extent, the steps comprising:

providing an elongate core extending axially along the distal portion of the prosthetic implant for reception within the recess in the natural bone, the core having an external surface with a transverse dimension less than the transverse extent of the internal surface of the recess for confronting the internal surface of the recess in the natural bone with the external surface spaced from the internal surface when the core is located within the recess;

providing at least one allograft body for placement along the core, over the external surface of the core; and placing at least the one allograft body for interposition between the core and the internal surface of the recess, the allograft body having a generally tubular configuration including an inner securement surface for gripping the core to secure the allograft body in place upon the core and an outer locator surface for engaging the internal surface of the recess to locate the core transversely within the recess.

17. The invention of claim 16 including placing at least the one allograft body on the core, and then engaging the outer locator surface with the internal surface of the recess to locate the core transversely within the recess.

18. The invention of claim 16 including:

providing a plurality of allograft bodies capable of placement along the core, over the external surface of the core; and selecting at least one of the plurality of allograft bodies for placement along the core; and placing the selected one of the plurality of allograft bodies for interposition between the core and the internal surface of the recess, the allograft bodies each having a generally tubular configuration including an inner securement surface for gripping the core to secure the selected allograft body in place upon the core and an outer locator surface for engaging the internal surface of the recess to locate the core transversely within the recess.

19. The invention of claim 18 including placing the selected one of the plurality of allograft bodies on the core, and then engaging the outer locator surface with the internal surface of the recess to locate the core transversely within the recess.

20. The invention of claim 18 wherein the relative transverse location of the inner and outer surfaces of at least one of the plurality of allograft bodies differs from the relative transverse location of the inner and outer surfaces of another of the plurality of allograft bodies , the invention including:

inserting the core into the recess subsequent to placing the selected one of the plurality of allograft bodies on the core; and selecting the transverse location of the core within the recess by selecting at least one of the plurality of allograft bodies and placing the selected allograft body on the core prior to insertion of the core into the recess.

21. In a method for implanting a femoral hip prosthesis within a recess in the natural bone of a natural femur, the femoral hip prosthesis having a proximal portion for enabling replacement of a femoral head, and a distal portion for securement within the recess, the recess including an internal surface having a transverse extent, the steps comprising:

providing an elongate core extending axially along the distal portion of the femoral hip prosthesis for reception within the recess in the natural bone, the core having an external surface with a transverse dimension less than the transverse extent of the internal surface for confronting the internal surface of the recess in the natural bone with the external surface spaced from the internal surface when the core is located within the recess;

providing at least one allograft body for placement along the core, over the external surface of the core; and placing at least the one allograft body for interposition between the core and the internal surface of the recess, the allograft body having a generally tubular configuration including an inner securement surface for gripping the core to secure the allograft body in place upon the core and an outer locator surface for engaging the internal surface of the recess to locate the core transversely within the femur.

22. The invention of claim 21 including placing at least the one allograft body on the core, and then engaging the outer locator surface with the internal surface of the recess to locate the core transversely within the femur.

23. The invention of claim 21 including:

providing a plurality of allograft bodies capable of placement along the core, over the external surface of the core; and selecting at least one of the plurality of allograft bodies for placement along the core; and placing the selected one of the plurality of allograft bodies for interposition between the core and the internal surface of the recess, the allograft bodies each having a generally tubular configuration including an inner securement surface for gripping the core to secure the selected allograft body in place upon the core and an outer locator surface for engaging the internal surface of the recess to locate the core transversely within the femur.

24. The invention of claim 23 including placing the selected one of the plurality of allograft bodies on the core, and then engaging the outer locator surface with the internal surface of the recess to locate the core transversely within the femur.

25. The invention of claim 23 wherein the relative transverse location of the inner and outer surfaces of at least one of the plurality of allograft bodies differs from the relative transverse location of the inner and outer surfaces of another of the plurality of allograft bodies, the invention including:

inserting the core into the recess in the femur subsequent to placing the selected one of the plurality of allograft bodies on the core; and selecting the transverse location of the core within the recess by selecting at least one of the plurality of allograft bodies and placing the selected allograft body on the core prior to insertion of the core into the femur.

26. A method for assembling a prosthetic implant having a proximal portion for enabling replacement of an element of a natural joint, and a distal portion for securement within a recess in the natural bone adjacent the natural joint, the recess including an internal surface having a transverse extent, the method comprising:

providing an elongate core extending axially along the distal portion of the prosthetic implant for reception within the recess in the natural bone, the core having an external surface with a transverse dimension less than the transverse extent of the internal surface for confronting the internal surface of the recess in the natural bone with the external surface spaced from the internal surface when the core is located within the recess;

providing at least one allograft body for placement on the core, over the external surface of the core;

placing at least the one allograft body on the core for interposition between the core and the internal surface of the recess, the allograft body having a generally tubular configuration including an inner securement surface for confronting the core and an outer locator surface for engaging the internal surface of the recess to locate the core transversely within the recess; and affixing the selected allograft body to the core.

27. The invention of claim 26 including:

providing a plurality of allograft bodies capable of placement on the core, over the external surface of the core; and selecting at least one of the plurality of allograft bodies for placement on the core; and placing the selected one of the plurality of allograft bodies on the core for subsequent interposition between the core and the internal surface of the recess, the allograft bodies each having a generally tubular configuration including an inner securement surface for gripping the core to secure the selected allograft body in place upon the core and an outer locator surface for engaging the internal surface of the recess to locate the core transversely within the recess.

28. A method for assembling a femoral hip prosthesis having a proximal portion for enabling replacement of a femoral head, and a distal portion for securement within a recess in the natural bone of a natural femur, the recess including an internal surface having a transverse extent, the method comprising: providing an elongate core extending axially along the distal portion of the femoral hip prosthesis for reception within the recess in the natural bone, the core having an external surface with a transverse dimension less than the transverse extent of the internal surface of the recess for confronting the internal surface of the recess in the natural bone with the external surface spaced from the internal surface when the core is located within the recess;

providing at least one allograft body for placement on the core, over the external surface of the core;

placing at least the one allograft body on the core for interposition between the core and the internal surface of the recess, the allograft body having a generally tubular configuration including an inner securement surface for confronting the core and an outer locator surface for engaging the internal surface of the recess to locate the core transversely within the femur; and affixing the selected allograft body to the core. the above amendments and the following discussion.

29. The invention of claim 28 including:

providing a plurality of allografts capable of placement on the core, over the external surface of the core; and selecting at least one of the plurality of allograft bodies for placement on the core; and placing the selected one of the plurality of allograft bodies on the core for subsequent interposition between the core and the internal surface of the recess, the allograft bodies each having a generally tubular configuration including an inner securement surface for gripping the core to secure the selected allograft body in place upon the core and an outer locator surface for engaging the internal surface of the recess to locate the core transversely within the femur.

* * * * *